US011058864B2

(12) United States Patent
Frost

(10) Patent No.: US 11,058,864 B2
(45) Date of Patent: *Jul. 13, 2021

(54) DEVICE AND A METHOD FOR PROVIDING RESUSCITATION OR SUSPENDED STATE IN CARDIAC ARREST

(71) Applicant: Neurescue ApS, Copenhagen S (DK)

(72) Inventor: Habib Frost, København V (DK)

(73) Assignee: Neurescue ApS, Copenhagen S (DK)

( * ) Notice: Subject to any disclaimer, the term of this patent is extended or adjusted under 35 U.S.C. 154(b) by 42 days.

This patent is subject to a terminal disclaimer.

(21) Appl. No.: 16/180,670

(22) Filed: Nov. 5, 2018

(65) Prior Publication Data
US 2019/0070348 A1 Mar. 7, 2019

Related U.S. Application Data

(63) Continuation of application No. 15/313,498, filed as application No. PCT/EP2015/061587 on May 26, 2015, now Pat. No. 10,143,789.

(30) Foreign Application Priority Data

May 26, 2014 (DK) .......................... PA 2014 70302
Oct. 31, 2014 (DK) .......................... PA 2014 70668

(51) Int. Cl.
A61M 1/10 (2006.01)
A61M 60/50 (2021.01)
(Continued)

(52) U.S. Cl.
CPC .............. A61M 60/50 (2021.01); A61F 7/12 (2013.01); A61H 31/007 (2013.01);
(Continued)

(58) Field of Classification Search
CPC .. A61M 1/1086; A61M 1/106; A61M 5/1723; A61M 1/1081; A61M 1/1006;
(Continued)

(56) References Cited

U.S. PATENT DOCUMENTS

| 4,077,394 A | 3/1978 | McCurdy |
| 4,280,494 A | 7/1981 | Cosgrove, Jr. et al. |

(Continued)

FOREIGN PATENT DOCUMENTS

| JP | 2002514472 | 5/2002 |
| JP | 200783038 | 4/2007 |

(Continued)

OTHER PUBLICATIONS

Tranmer, B. et al, "Intra-aortic balloon counterpulsation: a treatment for ischaemic stroke?", Neurol. Res., vol. 11(2), pp. 109-113, (Jun. 1989).

(Continued)

Primary Examiner — Scott M. Getzow
(74) Attorney, Agent, or Firm — McHale & Slavin, P.A.

(57) ABSTRACT

Disclosed is a device for providing resuscitation or suspended state through redistribution of cardiac output to increase supply to the brain and heart for a patient. The device includes an electrically controllable redistribution component attachable to the patient to provide redistribution of the cardiac output to increase supply to the brain and heart. The redistribution component, following a predefined reaction pattern based on an electrical signal, and computer means configured to: receive a patient data which identifies physiological and/or anatomical characteristics of the patent; and provide the electrical signal for the redistribution component based on the patient data or a standard response. The device may provide mechanisms to protect the aorta and the remaining anatomy of the patient from inadvertent (Continued)

damage caused by the disclosed device in any usage scenario of either correct intended usage or unintended usage. Also disclosed is a method for providing resuscitation or suspended state.

55 Claims, 11 Drawing Sheets

(51) Int. Cl.
| | | |
|---|---|---|
| *A61M 60/40* | (2021.01) | |
| *A61M 60/113* | (2021.01) | |
| *A61M 60/135* | (2021.01) | |
| *A61M 60/148* | (2021.01) | |
| *A61M 60/258* | (2021.01) | |
| *A61F 7/12* | (2006.01) | |
| *A61H 31/00* | (2006.01) | |
| *A61M 5/172* | (2006.01) | |
| *A61M 60/205* | (2021.01) | |
| *A61M 60/274* | (2021.01) | |
| *A61M 60/414* | (2021.01) | |

(52) U.S. Cl.
CPC ........ *A61M 5/1723* (2013.01); *A61M 60/113* (2021.01); *A61M 60/135* (2021.01); *A61M 60/148* (2021.01); *A61M 60/258* (2021.01); *A61M 60/40* (2021.01); *A61F 2007/126* (2013.01); *A61M 60/205* (2021.01); *A61M 60/274* (2021.01); *A61M 60/414* (2021.01); *A61M 2205/054* (2013.01); *A61M 2205/071* (2013.01); *A61M 2205/3334* (2013.01); *A61M 2205/3375* (2013.01); *A61M 2205/3379* (2013.01); *A61M 2205/3507* (2013.01); *A61M 2205/50* (2013.01); *A61M 2205/502* (2013.01); *A61M 2205/52* (2013.01); *A61M 2205/581* (2013.01); *A61M 2205/587* (2013.01); *A61M 2205/702* (2013.01); *A61M 2205/8206* (2013.01); *A61M 2230/005* (2013.01); *A61M 2230/04* (2013.01); *A61M 2230/30* (2013.01); *A61M 2230/43* (2013.01); *A61M 2230/50* (2013.01)

(58) Field of Classification Search
CPC .... A61M 1/1072; A61M 1/125; A61M 1/122; A61M 1/1046; A61M 1/101; A61M 1/107; A61M 1/1034; A61M 2230/50; A61M 2230/43; A61M 2230/30; A61M 2230/04; A61M 2230/005; A61M 2205/8206; A61M 2205/702; A61M 2205/587; A61M 2205/581; A61M 2205/52; A61M 2205/502; A61M 2205/50; A61M 2205/3507; A61M 2205/3379; A61M 2205/3375; A61M 2205/071; A61M 2205/054; A61M 2205/3334; A61M 2210/125; A61M 2205/3344; A61H 31/007; A61F 7/12; A61F 2007/126
See application file for complete search history.

(56) References Cited

U.S. PATENT DOCUMENTS

| | | | |
|---|---|---|---|
| 5,195,942 | A | 3/1993 | Weil et al. |
| 5,413,558 | A * | 5/1995 | Paradis ............ A61B 17/12045 600/18 |
| 5,820,593 | A * | 10/1998 | Safar .................. A61M 1/3621 604/96.01 |
| 6,231,551 | B1 | 5/2001 | Barbut |
| 6,312,399 | B1 | 11/2001 | Lurie et al. |
| 8,177,704 | B1 | 5/2012 | Mohl et al. |
| 2005/0209579 | A1 | 9/2005 | Yacoubian et al. |
| 2006/0064059 | A1* | 3/2006 | Gelfand ............... A61B 5/0215 604/103.06 |
| 2010/0163023 | A1* | 7/2010 | Singh ................. A61M 16/0438 128/200.26 |
| 2011/0295177 | A1 | 12/2011 | Mohl |
| 2011/0295302 | A1 | 12/2011 | Mohl |
| 2012/0165853 | A1 | 6/2012 | Paulussen et al. |
| 2013/0102926 | A1* | 4/2013 | Eliason ............... A61B 5/1076 600/585 |
| 2013/0178711 | A1 | 7/2013 | Avneri et al. |
| 2014/0243873 | A1 | 8/2014 | Franklin |

FOREIGN PATENT DOCUMENTS

| | | |
|---|---|---|
| JP | 2010502313 | 1/2010 |
| WO | WO2008028149 | 3/2008 |
| WO | WO2011085166 | 7/2011 |
| WO | WO2011085180 | 7/2011 |
| WO | WO2014134215 | 9/2014 |
| WO | WO2015035393 | 3/2015 |

OTHER PUBLICATIONS

Internet Article, "Intra-aortic balloon pump", https://lifeinthefastlane.com/cc/intra-aortic-balloon-pump/, retrieved Mar. 17, 2017, pp. 1-12, (Jan. 14, 2014).

* cited by examiner

Native flow

Retrograde flow towards brain and heart

Free Flow

Occlusion

DEVICE AND A METHOD FOR PROVIDING RESUSCITATION OR SUSPENDED STATE IN CARDIAC ARREST

CROSS REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 15/313, 498, entitled "A DEVICE AND A METHOD FOR PROVIDING RESUSCITATION OR SUSPENDED STATE IN CARDIAC ARREST", filed Nov. 22, 2016, which is a § 371 national stage entry of International Application No. PCT/EP2015/061587, entitled "A DEVICE AND A METHOD FOR PROVIDING RESUSCITATION OR SUSPENDED STATE IN CARDIAC ARREST", filed May 26, 2015, which claims priority of Denmark Patent Application No. PA 2014 70302, filed May 26, 2014 and Denmark Patent Application No. PA 2014 70668, filed Oct. 31, 2014, the entire contents of which incorporated herein by reference.

FIELD OF THE INVENTION

The invention relates to devices and methods for providing resuscitation or suspended state in cardiac arrest, e.g. to increase return of spontaneous circulation (ROSC) or to expand the time window of intervention to enable new opportunities for diagnostics and treatments for patients in cardiac arrest.

BACKGROUND OF THE INVENTION

Cardiovascular disease contributes 30.9% of global mortality. Currently only 1 out of 10 survive a cardiac arrest to hospital discharge. It is responsible for higher mortality rates than any other disease in industrialized countries, and three-quarters of non-infectious mortality in developing countries. In the US there are around 350.000 cardiac arrests outside of hospitals; and at least as many inside hospitals. The potential for improvement is massive. In 2010, the cost of medical care for heart disease in the US was $273 billion and the loss in productivity was $172 billion.

By the early 1970s, CPR (Cardiopulmonary Resuscitation), defibrillation, and prehospital care were all in place. The introduction of automated defibrillation units (AED) expanded the possibility for prehospital treatment of cardiac arrest, and the first AED was successfully put to use by paramedics in Brighton in 1980. In spite of this, our current best practice only has the ability to achieve resuscitation, return of spontaneous circulation (ROSC), for around 25-30% of patients both in pre-hospital and in-hospital settings.

There is a change in the characteristics of the population suffering cardiac arrest. Ten years ago, broad population studies showed that around 70% of people suffering cardiac arrest had initial shockable rhythms (ventricular fibrillation or ventricular tachycardia) as the first documented electrocardiographic rhythm. Today, multiple large population studies note that only 20% to 30% of those suffering a cardiac arrest have a shockable rhythm as their initial rhythm.

The defibrillator is far from effective for everyone, even when stratifying for presenting rhythm. Roughly stated electricity cannot open an occluded coronary artery. There is rarely enough time to diagnose and treat the underlying cause of the cardiac arrest, and even defibrillation depends on optimizing hemodynamic variables beforehand. From other patient settings we know of and perform time-consuming treatments that could save the patients life but cannot currently be performed within the time constraints of a cardiac arrest.

This change in initial arrhythmia also has wide implications. We can try to defibrillate a shockable rhythm, but we have no truly effective treatments otherwise.

CPR and Defibrillation have been basically unchanged since their implementation. CPR cannot generate sufficient cerebral blood flow to preserve normal cerebral viability until cardiac function is restored. This explains why cardiac arrest has such high neurological morbidity and mortality. Therefore, we need new methods to improve cerebral blood flow and subsequent neurological outcome from cardiac arrest, especially if we want to do more efforts than defibrillation. Even if only defibrillation is performed, new methods to improve coronary blood flow can improve the likelihood of success from defibrillation.

As an example, coronary artery disease represents the most common cause of out-of-hospital cardiac arrest, but the treatment, percutaneous coronary intervention (PCI), cannot to be performed within the time limits of current CPR. Alternatively, even treatments of fibrinolytics and CABG (coronary artery bypass graft surgery), takes too long time to perform in a cardiac arrest.

Cooling (therapeutic hypothermia) has only proved useful in the patients that achieve a return of heartbeat, so-called ROSC (return of spontaneous circulation), and do not alter the proportion of those who achieve ROSC or not. Cooling slows down the cellular requirement, lowering the need to match the lowered supply—e.g. cerebral metabolic demands lower by about 8% per degree Celsius drop in temperature—but it usually takes hours to reach the desired temperature and is therefore not an effective way to bridge the patient in cardiac arrest to definitive treatment. By then, the patient is already irreversibly and totally neurologically damaged.

Late therapy like cardiopulmonary bypass or ECMO (extracorporal membrane oxygenation) devices, no matter how good, is never effective once the ischemic capability of the heart and brain is exceeded. Nevertheless, recovery may be improved by these devices, which unfortunately cannot be initiated fast enough in cardiac arrest to replace the need for an intermediate suspended state device.

Continued cardiac arrest will result in metabolic acidosis. Here e.g. sodium bicarbonate can maintain blood pH and plasmapheresis can clear the build-up of toxins.

OBJECTS OF THE INVENTION

It is an object of embodiments of the invention to provide a device or a system that enables blood redistribution in a patient suffering from cardiac arrest, so as to render heart massage (chest compression) more effective in maintaining the vital perfusion of the CNS. It is a further object of embodiments of the invention to provide a method for providing resuscitation or suspended state in a cardiac arrest patient. It is also an object of embodiments of the invention to provide a device and a method by which ease-of-use and a built-in safety can withhold the potentially damaging effect of a cardiac output redistribution method and thereby enable methods for providing suspended state or immediate resuscitation. It is a further object to provide a device and a method by which a patient can be placed in suspended state in both the near-community and hospital settings, in hands of users with minimal training, to thereby allow not only in-hospital specialists but also prehospital health care professionals and others to carry out such procedures to thereby achieve a marked expansion of the time window to reverse a cardiac arrest, or improve the likelihood of success from immediate defibrillation.

Particularly, it is an object of embodiments of the invention to enable the delivery of diagnostics and treatments that cannot currently be delivered to the patient in cardiac arrest, where almost universally only defibrillation and drug administration can be achieved within the current window of intervention of around 10-30 minutes.

SUMMARY OF THE INVENTION

It has been found by the present inventor that a main problem during cardiopulmonary resuscitation (CPR) of cardiac arrest patients is the fact that non-vital organs and tissues are perfused and supplied with oxygen at an—under these circumstances—unnecessary high level and that this happens at the expense of the CNS, in particular the brain, and the heart, which in contrast to these non-vital organs and tissues are highly sensitive to low oxygenation. Further it has been found by the inventor that if this imbalance during CPR could be changed to favour the perfusion of the CNS and the heart, then the chances of survival of these patients would be greatly enhanced.

However, it is normally necessary to perform a surgical intervention in order to establish preferential perfusion of the brain and heart in a patient and this surgical intervention requires the skills of a surgeon. On the other hand, staff of rescue teams is normally not surgeons so it is hence advantageous to be able to provide a device or systerri, which via a very simple intervention—which does not require surgical skills—can bring about the advantageous preferential perfusion of brain and heart.

The present inventor has hence realized a novel technological appliance and new methods. Unlike cooling (also referred to as 'suspended animation'), were the metabolism in the cells is slowed down considerably, which cannot be initiated fast enough if the cardiac arrest has already occurred, we wish to introduce a new term of 'suspended state', where the neurological damage process itself is put to a halt, by controlled redistribution of the cardiac output from chest compressions to the brain and heart—to create an increasing metabolic debt to the tissues that can tolerate this state, thus still keeping every single cell in the body viable. The use of a supraceliac aortic occlusion can increase the coronary and cerebral perfusion pressure with about a 100%, thus reaching viable levels again. We can extrapolate this from the use of cross clamps in surgical correction of aortic aneurysms, from the use of simple surgical balloon catheters in e.g. aortic aneurysm graft expansion and in the care of pelvic and truncal traumas, and that the remaining organs can tolerate this intervention for some time.

The use of vasodilator drugs can have a substantial impact on lowering the restriction on perfusion delivered to the brain and heart. For the first time we want to propose the use of a cardiac arrest aortic occlusion balloon therapy being used together with the addition of high-potency vasodilators, hereunder sodium nitroprusside or high-dose nitro-glycerine, to create a high-flow state to the brain and heart with low microcirculatory resistance, while at the same mitigating the systemic vascular collapse caused by the vasodilator through the use of the aortic occlusion balloon.

Using this one or several abovementioned in a new bridge therapy could carry patients in cardiac arrest directly to definitive treatment methods, or to an intermediate intervention such as hypothermia or ECMO and subsequently to definitive treatment methods. However, these devices and methods will remain theoretical curiosities, if we do not also invent ways of putting them in the hands of the doctors, paramedics and nurses, that deliver the first-aid for patients in cardiac arrest, and not only in the hands of our specialist physicians in the receiving hospital departments. Alternatively the proposed methods can be used to increase the immediate resuscitation chances from e.g. defibrillation.

The population who suffers from cardiac arrest very often suffers from comorbid aortic atherosclerosis making the aorta fragile, brittle and porcelain-like. This makes it necessary to invent intelligent safe ways in which the redistribution can be carried out while protecting the anatomy of the patient to the maximum possible extent. The use of external abdominal aortic binding or compression as an alternative to an endovascular technique is therefore not without substantial risk and can lead to e.g. plaque rupture, dissection, wall rupture, or thromboembolic incidences.

On the other hand, leading a balloon catheter blindly without careful control of where and when the balloon exercises its pressure can lead to damage on the patient's anatomy, especially in the stressful situation of a cardiac arrest. If only verified by human estimation, the balloon catheter could inadvertently, how rare these incidences might occur, end in e.g. an arterial branch of the aorta, in a venous vessel side of the vascular system, in a dissection between layers of the aortic wall or in a tissue compartment outside of the vascular system.

To improve the existing methods for redistribution, and to enable safe redistribution for non-medical practitioners or semi-skilled practitioners, e.g. for rescue teams etc. the present invention hence provides in a first aspect a device or system for providing resuscitation or suspended state through redistribution of cardiac output to increase supply to the brain and heart for a patient, the device comprising
    an electrically or manually controllable redistribution component attachable to the patient and being configured to interact with the patient to provide redistribution of the cardiac output to increase supply to the brain and heart, the redistribution component following a predefined reaction pattern based on an electrical signal, and
    computer means configured to:
      receive a patient data which identifies physiological and/or anatomical characteristics of the patient; and
      provide the electrical signal for controlling the redistribution component and/or for presenting the physiological and/or anatomical characteristics for a user based on the patient data or a standard response.

When automatically operated, the redistribution operates in a predefined value, e.g. based on universal threshold values not directly connected to a specific patient, but the same may be attained if using manual operation—in that case the redistribution is controlled manually (e.g. by manually controlling an occlusion device, e.g. a balloon) in response to the measured values. Due to the electrically or manually controllable redistribution component and the ability of the computer means to receive patient data, the device can enable a redistribution taking the individual's actual aortic specifications into account. In this process, the ability of the computer means to provide electrical signals for the redistribution component (or for a device presenting data to the operator thereof) enables control of the redistribution component directly based on the received patient data and the predefined reaction pattern. Accordingly, the device facilitates a safe procedure in which a computer interacts with the patient based on knowledge on not only the patient but also knowledge regarding the redistribution component. According, the intervention can be predictable and repeatable compared to the procedure carried out manually based on an intuitive understanding of the patient.

For instance, the device can take the actual placement of a catheter head into account, whether the catheter is in an intended position or has ended in an unintended position, withholding occlusion.

The term "redistribution" is in the present context intended to mean an intervention (preferably mechanical) that ensures that the cardiac output is preferentially directed to the brain and the heart in order to supply these two organs with sufficient perfusion of blood at the expense of perfusion of other organs that are not highly supply sensitive over a limited time span.

The term "suspended state" is meant to denote a state in a cardiac arrest patient who is undergoing treatment, where neurological damage processes are put to a halt by controlled redistribution.

The term "to bridge" is in the present context intended to mean an allowance to expand the time window of intervention for the patient to allow time for diagnostics and treatments and/or as an allowance to transport the patient from one physical location to another and/or an allowance to transfer the patient between the care of different professional groups of people.

The term "attachable" is in the present context intended to mean a tissue-device connection that allows for an interface of one the following: Outside a patient, onto a patient, through a puncture or surgical site and an interface that is implanted inside the patient.

Due to the combination between an electrically or manually controllable redistribution component and the computer means configured to provide the electrical signal based on the patient data, the device according to the invention becomes capable of facilitating a risk-mitigating factor.

The electrically or manually controllable redistribution component is attachable to the patient such that its interaction becomes independent of user error. Examples of redistribution components include aortic balloons, patient tilting devices and any other device, which is capable of providing blood redistribution in the patient.

An alternative to the use of such component is a redistribution component, which comprises or consists of an aortic retrograde perfusion pump. Relatively large volumes of aerated blood may be present in the peripheral vessels and making this blood volume accessible to the heart and brain can significantly increase the chances of survival.

The redistribution component can interact with the patient to provide redistribution of the cardiac output by following a predefined reaction pattern that means that a specific control signal provides a well-known and expected result. In that way, the electrical signal provided by a computer based on patient data enables a safer and more predictable treatment.

The computer means may include memory means, e.g. in the form of a so-called flash memory or similar computer memory containing re-definable data or fixed data. The memory means may include a predefined definition of the electrical signal as a response to the patient data.

In one example, the predefined definition is a function determining the electrical signal or a representation of the electrical signal as a function of the patient data, and in another example, the predefined definition is in the form of a table containing a representation of the electrical signal for corresponding patient data.

The patient data may e.g. include parameters selected from the group consisting of: aortic blood pressure, aortic blood flow, duration of cardiac arrest, expiratory $CO_2$, ECG, blood pressure, compression rate and depth, pulse, respiratory frequency, cardiac output redistribution degree, aortic $O_2$ saturation or concentration, cerebral or peripheral saturation, temperature, fluid administered, pharmaceuticals administered, biochemical data and ultrasound imaging.

The electrical signal may control function of the redistribution which in a controlled manner influence the patient and which is reflected in the patient data.

The device may further comprise patient data generation means configured to generate patient data during external cardiac compression carried out on the patient, the patient data generation means configured to generate the patient data by sensing biosignals from the patient. Examples of such biosignals are aortic pressure e.g. generated during cardiac compression (heart massage) or aortic blood flow e.g. generated during cardiac compression.

Accordingly, the patient data generation means may be configured to sense biosignals from a blood vessel or a tissue compartment. The patient data generation means may include one or more pressure and/or flow sensors including e.g. traditional pressure sensors and flow measuring devices of the kind known in the art.

In one embodiment, the redistribution component comprises an aortic expansion member, e.g. an aortic balloon with electrically or manually controlled inflation and/guiding means for positioning of the balloon in the aorta and being capable of expanding e.g. upon introduction of an expansion fluid medium. In other words the inflation means can be adapted to be capable of being operated manually by a user; this will normally require that the user is informed by the device about the values that the automated version of the device receives. However, in the most user-friendly versions of the device/system of the inflation means is adapted to be capable of being operated automatically.

Particularly, the redistribution component may comprise an elongated body extending between a proximal end and a distal end. Herein, the distal end is that end which is insertable into the patient, and the proximal end is that end which is left outside the patient. The redistribution component may further comprise inflation means connected to the aortic expansion member for expanding the aortic expansion member, e.g. a traditional pump such as a roller or piston pump for pumping a fluid medium into the expansion member.

The expansion fluid medium could be a liquid or gaseous substance, e.g. a saline solution or helium.

The device may further comprise an adaptable tissue protection mechanism configured to:
determine a blood pressure or blood flow present in a blood vessel of the patient during cardiac compression;
determine an aortic expansion member characteristics defining a degree of expansion of the aortic expansion member based on the determined blood pressure or blood flow; and
to provide an electrical signal for controlling the inflation means in accordance with the determined aortic expansion member characteristics.

The expansion member characteristics may e.g. be the pressure inside the expansion member, it may be a volume of the expansion fluid medium, which is introduced into the expansion member, or it could be represented by a degree of deformation of the expansion member etc.

The adaptable tissue protection mechanism could be configured to determine the aortic expansion member characteristics based on the determined blood pressure or blood flow multiplied by a predetermined factor, e.g. a factor being in the range of 1.0-1.2 times the pressure of the blood in the aorta during cardiac compression.

If the redistribution component is an aortic expansion member, the electrical signal may e.g. specify a degree of expansion, a timing of expansion, i.e. when the expansion member should be expanded, duration of expansion of the aortic expansion member, and/or a timing of contraction of the aortic expansion member—i.e. when the expansion member should be contracted to allow blood flow across the expansion member to thereby reduce the degree of redistribution of the cardiac output.

The device may therefore comprise means for specifying a degree of expansion of the expanding member, means for timing of the expansion, means for determining duration of expansion, and/or means for timing of contraction of the expanding member. In one embodiment, any of these means are controlled based on the patient data in combination with the above-mentioned pre-defined definition of the electrical signal.

The device may further comprise a location safety mechanism comprising at least one first sensor capable of determining a biosignal that is characteristic for the aorta of the patient and an electronic circuit configured to verify a position of the expansion member in the aorta based on the biosignal. The at least one first sensor may e.g. comprise a pressure sensor or a flow sensor or a force sensor or any other sensor of the biosignals discussed herein.

The first sensor could be located on the redistribution component to determine the biosignal in a position distal to the aortic expansion member. Typically, this means located either in a position distal to the aortic expansion member or in connection to a member positioned distal the aortic expansion member.

The device may be configured to use data from the first sensor in combination with data from sensors located at other locations, e.g. at least one other sensor located to determine the biosignal in a position proximal to the aortic expansion member, e.g. a sensor attached to the redistribution component. Typically, this other sensor would be placed caudal to the first sensor.

The data from the first and other sensors could be diastolic or systolic blood pressure or it can be pressure, force, distance, width, volume and/or flow.

The location safety mechanism may be configured to determine whether the aortic expansion member is located in a position selected from a group consisting of: a pulsating vessel in accordance with being the aorta of the patient, a pulsating vessel not in accordance with being the aorta, a pulsating vessel being indeterminate as the aorta of the patient, a venous vessel, a tissue compartment not being a blood vessel, a tissue compartment indeterminate in location. As an example, the location safety mechanism may thereby determine if the aortic expansion member is located in a renal artery, in tissue outside a blood vessel, in a blood vessel not being the aorta, and to determine when it is positioned, as desired, in the aorta.

The device may further comprise a second sensor inside the aortic expansion member or proximal to the expansion member.

The device may be configured with a feedback loop receiving data from at least one of the first and second sensor, to control the filling of the aortic expansion member. The feedback loop may e.g. be capable of controlling flow, volume, distance, width, force and/or pressure of the aortic expansion member, hereunder the filling of the member to reach a pressure that is the result of a standard the multiplication of the pressure sensed above the member and a predefined factor or interval.

The device may further comprise a first failsafe mechanism, configured to determine a pressure in the aortic expansion member and to determine a volume of the aortic expansion member, to determine a ratio between the pressure and the volume, and to compare the ratio with an upper and lower threshold value, and to execute a control sequence including stopping of further inflation of the aortic expansion member or deflation of the aortic expansion member.

The control sequence could be carried out during a period of e.g. 10-20 seconds or longer. Alternatively, the filling is immediately stopped, or alternatively immediately reverted, due to a concern that the member might not be in the right vessel or tissue compartment.

The device may further comprise a user interface for use of selectable operation of the inflation means, e.g. a control button which controls operation of the inflation means directly such that the medical practitioner can initiate inflation or deflation of the expansion means at will.

The device may comprise a halt interface allowing manually selectable deflation of the aortic inflation member, and the halt interface may be configured to execute the deflation over a period of time, such as a predefined number of seconds, e.g. over 1-10 or more seconds. This may cause a smoother and less stressing deflation and thus protect the heart function of the patient.

The device may comprise a patient state monitor configured to determine a biosignal representing Return of Spontaneous Circulation (ROSC), and to control deflation of the aortic expansion member based on the determined signal.

The device may further comprise an electronic human interface with a graphical or audio user interface configured to provide instructions or information related to the location and degree of filling of the aortic expansion member in the aorta of the patient. The user interface may e.g. be a graphical and/or audible user interface configured to provide instructions related to placement of the aortic expansion member in aorta of the patient and device and patient status feedback. E.g. "Filling underway"; "Balloon occlusion successful" or "Catheter head is outside of the aorta. Retract and try again". If the redistribution component and/or occlusion means is manually operated the instructions provided may be more detailed and can e.g. provide details about the status of the redistribution efforts to the user.

The device according to the invention may provide the anatomical verification of placement of the expansive member in an arterial vessel by the use of at least one sensor for determining pressure, flow and/or volume data significant for pressure, flow and/or volume of a fluid inside the expansive member or inside a blood vessel or tissue of the patient.

The user interface may communicate with the sensor, and based on signals from the sensor, the device may determine a plausible position of the expanding member in the body of the patient and provide user instructions via the electronic human interface based on the plausible position.

The computer means may e.g. be configured to compare the pressure; flow and/or volume data with reference input data and based on the comparison to verify a position of the aortic expansion member in the body. I.e. when the expansion member is in an intended position in the aorta, the corresponding pressure, flow and/or volume data should be within a certain expected upper and lower limit. If it is outside of this expected limit, the user may be notified that the expansion member is possibly not in correct position or approximated damaging the patient and was therefore stopped. Should the device find another position which corresponds to the determined pressure, flow and/or volume data, the user may be notified, e.g. by a graphical representation of the aorta and the expansion member, which position appears to be the actual position. Thus the device of the invention may comprise an interactive human user guide configured to provide information related to a position of the aortic expansion member in the patient, the information being determined based on the pressure, flow and/or volume data.

The computer mean can then determine the size and type of blood vessel by analysing the pressure, flow and/or volume data continuously, and activate a failsafe for some verified positions in the body, thereby stopping the redistribution component interaction with the patient.

The computer means can use the input data to determine and deliver the lowest needed impact from the aortic expansion member to accomplish the redistribution and carry out said redistribution.

The invention may thus provide a device with a built-in safety mechanisms for verification of the intervention, to withhold the potentially damaging effort, the expansion of an occlusion balloon within a patient, when and where it ought not to happen—To put the technology of 'suspended state' in the hands of trained first-responders, not only physicians. This will enable a new intervention that spearheads new opportunities for treatment that is not possible within the current time window of 10-30 minutes. The time-expanding intervention would be initiated in a cardiac arrest once initial defibrillation and drug treatment prove useless.

Particularly, the device may be used in e.g. the following protocol, which specifies:

1) Initiate and continue either manual or automatic chest compressions, possibly preceded by administration of tissue protectant e.g. recombinant human erythropoietin. 2) Attempt defibrillation of the patient. 3) Cardiac arrest won't revert. Decision to use safe device for aortic occlusion. 4) Turn on device. Administer safe aortic occlusion through device mechanisms. 5) Attempt to defibrillate the patient again with the improved hemodynamics after the occlusion. 6) If unsuccessful, potential administration of a vasopressor, e.g. vasopressin. This is a clinical decision based on presumed cause of arrest e.g. anaphylaxis. Repeat administration periodically. Potential administration of a vasodilator, e.g. sodium nitroprusside. This is a clinical decision based on presumed cause e.g. refractory coronary artery disease. Potential periodic repetition of either drug and/or administration before use of Device. 7) Cardiac arrest won't revert=>Decision to put patient in suspended state. 9) Potential application of 30-90 degree head down or head up tilt. 10) Potential application of intravascular 2 degree Celsius saline solution, surface cooling pads on body, hypothermic total liquid ventilation and/or administration of muscle relaxant. 12) Potential administration of a vasodilator, e.g. sodium nitroprusside, to improve suspended state microcirculation. Potential periodic repetition of vasodilator administration. 13) Transport to Specialist Center. 14) Initiate in-hospital cardiopulmonary bypass, ECMO or deliver e.g. PCI-treatment directly. 15) Potential plasmapheresis or dialysis. 16) Achieve return of patient heartbeat with other means possible. 17) Continuation of cooling for additional 24 hours after return of heartbeat. 18) Prognosticate the patient after at least 72 hours of sustained therapy. 19) Continuous monitoring of treatment with e.g. end-tidal $CO_2$, aortic pressure or trend-NIRS measurement, attached from the very beginning to evaluate efforts.

To further increase the safety and to provide improved information e.g. related to the position of the aortic expansion member in the body, the device may comprise means for ultrasound imaging. Data from such means may be used for guidance of the user.

If the aortic expansion member is an aortic occluding balloon, the device may comprise means for filling the aortic occluding balloon with a liquid, e.g. with saline, or a gas, including e.g. helium or $CO_2$, and measuring the aortic pressure and balloon pressure. In an interesting embodiment, the device further comprises a handheld unit comprising the computer means and the filling means and being attachable to the aortic occluding balloon. In another interesting embodiment, the device further comprises a human interface unit comprising the filling means and being attachable to the aortic occluding balloon, said human interface optionally being attachable in a fixed position on a patient and wherein said human interface is optionally integrated with the human interface described above or with the handheld unit. In both cases, the aortic occluding balloon can be pre-attached to the handheld unit.

The computer means could be configured not only to communicate the electrical control signals to the redistribution component but also to receive input data from the redistribution component. The redistribution component may include a sensor function e.g. specifying faults, or providing data relevant for controlling the redistribution component. Such data may include data indicating a lack of expansion, use of the redistribution component, e.g. the number of expansions and contractions, which have been attained.

The device may further comprise a component attachable to the patient and being configured to administer fluids and drugs to the patient. The administering of such fluids and drugs may be controlled by the computer means of the device, and feedback regarding the administration of the fluids or drugs may be provided via the aforementioned electronic user interface.

The component for administering fluids and drugs to the patient may e.g. be configured for administering timed and controlled amount of fluids and/or drugs.

The device may further comprise additional components, e.g. components from the group consisting of: a patient monitor, a vitals signs monitor, a watch, an external chest compression device, a respirator, an ECG monitor, a defibrillator, a pacemaker, a pH measurement device, an ultrasound device, an ECMO/ECLS device, a body cooling device, an infusion pump, a capnograph, a ventricular assist device, a dialysis device, touchscreen and a telecommunications device. An interesting embodiment, when the device integrates a defibrillator is to include in the catheter carrying the occlusion device at leas one electrode that allows the establishment of a voltage difference between the catheter (i.e. the interior of a vessel such as the aorta) and an external electrode, e.g. place on the anterior chest wall.

The redistribution component may comprise means for tilting the patient in a head down tilt orientation or for tilting the patient in a head up position. The first may provide a sometimes advantageous increase in blood pressure in the redistribution compartment, whereas the latter may alleviate the resistance against the venous blood leaving the brain and heart. Both of these may be advantageous for a patient in a redistributed state depending on how the patient's physiology presents itself in this new type of treatment.

The device may further comprise means for a self-test system, double circuitry, and usage event data recording.

In interesting embodiments the device of the invention is able to receive a signal of, or being able itself sense that the patient is in a state of cardiac arrest or reduced cardiac output, the device being able to respond to that state with an increase in blood flow and/or pressure towards the cranial side of the patient, through a separate member, or through a part of the device being intravascular. In other words, in this embodiment the device is adapted to be permanently present (implanted) in a patient (typically a patient likely to suffer from cardiac arrest). In this embodiment, the device can respond to a decrease in blood pressure and/or blood flow and/or heart rate and/or any other relevant indication of cardiac arrest and automatically effect redistribution of cardiac output so as to preferentially supply the heart and brain. It is especially preferred in this embodiment that the device acts in coordination with e.g. a cardiac pacemaker or other implanted devices in order to further enhance chances of survival. Conveniently, the device is capable of signalling to an external source that the patient is said state, e.g. to alert EMS to locate and attend the patient.

During insertion, there may exist a safety risk if each procedure step is not carried out correctly and finalized before the next procedure begins. Particularly during insertion of the aforementioned elongated body constituting in one embodiment the redistribution component, it is of particular importance to ensure a systematic insertion approach.

Accordingly, the device may comprise an aortic detection and puncture means configured for attachment to the patient and being configured to operate in at least five distinct operation phases including a vessel detection phase, a vessel puncture phase, a vessel insertion phase, a catheter dilatation phase, and a confirmation phase. Data related to one phase may be stored and used subsequently when carrying out the next phase.

The computer means of the device/system of the invention may be adapted to communicate with at least one other therapeutic and/or monitoring device so as to allow coordination of the operation of said therapeutic devices and the device according to any one of the preceding claims. This at least one other therapeutic and/or monitoring device is preferably selected from a cardiac resynchronization therapy device, a cardioverter-defibrillator, and a cardiac pacemaker.

METHODS OF THE INVENTION

As will be apparent from the claims, the presently described device is useful in methods for providing resuscitation or suspended state in a human cardiac arrest patient, said method comprising subjecting the patient to heart massage (chest compression which may be manual or accomplished by use of a mechanical chest compression device) while at the same time ensuring redistribution of the cardiac output to preferentially supply blood to the brain and the heart; these methods that are detailed in the claims need not necessarily utilize the device of the invention as will also be apparent from the claims.

In said method, the redistribution is typically accomplished by at least one of the following:
 occlusion of the aorta caudal to the left subclavian artery;
 head-down or head up tilting of the patient so as to reach an angle of between 30 and 90 degrees relative to the horizontal plane;
 applying an external compression force onto the abdomen and/or thigh(s) and/or arm(s) so as to reduce the perfusion distal to the external compression force;
 passively raising the legs to reach an angle between 30 and 90 degrees relative to the horizontal plane.

The method may be combined with at least one of the following treatments of the patient:
 administration of fluids, including saline and buffers such as bicarbonate,
 administration of vasopressive drugs, including vasopressin and analogues,
 administration of a tissue-protecting agent, such as erythropoietin;
 administration of anti-arrhythmic drug, such as amiodarone;
 reduction of body temperature, such as by use of cold IV-fluid infusion, cooling catheters, transnasal evaporative cooling, extracorporeal cooling or total liquid ventilation with temperature controlled perfluorocarbons. This may be done repeatedly, optionally according to a fixed sequence.

The method according preferably comprises that redistribution is accomplished by occlusion of the aorta caudal to the left subclavian artery and even more preferred by use of a device of the invention for this purpose. For instance, occlusion can be accomplished by introducing a device of the present invention into the aorta, preferably via the femoral artery, and subsequently decreasing or interrupting the blood flow distal to the redistribution component by expanding the redistribution component of said device. In this embodiment it is preferred that the redistribution component is expanded in a controlled manner in response to measurement(s) that indicate the degree of occlusion and correct placement of said device in the patient's aorta. As indicated above in the discussion of the device of the invention, this occlusion and placement may be fully automated or manually operated. The measurements are typically selected from the group consisting of:
 duration of expansion redistribution component usage;
 blood flow passing by the redistribution component;
 blood pressure distal of the redistribution component, optionally combined with blood pressure proximal to the redistribution component;
 aortic $O_2$ saturation distal of, and preferably in close proximity to, the redistribution component, optionally combined with arterial $O_2$ saturation proximal of the redistribution component.

It is preferred that expansion of the redistribution component is controlled manually or by the computer means of the device to avoid incorrect positioning or expansion degree of said device and by activating the failsafe of claim 9 in case said device is verified to be incorrectly positioned thereby interrupting the expansion of the redistribution component to allow subsequent correct positioning. In broad terms, the method preferably includes means and measures that avoid incorrect redistribution of blood flow.

In certain embodiments redistribution is temporarily interrupted at regular or irregular intervals so as to ensure sufficient perfusion of all parts of the body of the patient. However, some caution must be exercised due to spontaneous dilation of blood vessels in the non-perfused part of the body during the redistribution, meaning that reestablishment of the redistribution state can be difficult.

The method of the invention may act during or as a bridge to one or more of therapeutic hypothermia; angioplasty, including PCI and angiography; dialysis; administration of drugs such as vasopressors, thrombolytic drugs such as fibrinolytics, fluids, bicarbonate, antidotes, and antiarrhythmic drugs; the use of ultrasound, X-ray, CT, or MR; intubation; mechanical ventilation; ventricular assist devices;

heart transplantation, including artificial heart transplantation; surgery, including CABG surgery and valve surgery; blood transfusion; placement of external or internal pacemaker or ICD; catheter ablation; thromboendarterectomy; defibrillation; transportation; ECMO; ECLS and cardiopulmonary bypass. In other words, the method may be combined with any one of a number of other methods that are commonly used in resuscitation.

The method may further comprise that the restriction on perfusion delivered to the brain and heart is lowered through the use of a vasodilator, hereunder specifically sodium nitroprusside or nitroglycerin and repeated administration of sodium nitroprusside or nitroglycerin, hereunder repetition in intervals of 2-10 minutes. This may be combined with the use of an aortic expansion member to prevent the systemic vascular collapse caused by the vasodilator.

The method of the invention can also be combined with the use of any one of the following: active compression-decompression CPR, an impedance threshold device, adenosine administration, controlled pauses in the CPR (e.g. compressions for 20 seconds, then a pause in compressions for 20 seconds.)

A related method of the invention for providing resuscitation or suspended state through redistribution of cardiac output to increase supply to the brain and heart for a human in cardiac arrest or imminent cardiac arrest comprises subjecting the patient to external chest compression while at the same time ensuring redistribution of the cardiac output accomplished by occlusion of the aorta caudal to the left subclavian artery, and comprising lowering the restriction on perfusion delivered to the brain and heart through the use of a vasodilator, hereunder specifically sodium nitroprusside or nitroglycerin, hereunder repetition in intervals of 2-10 minutes. Also this method may act as a bridge to one or more of the following:

ECMO; ECLS; cardiopulmonary bypass; angioplasty, including PCI and angiography; dialysis; therapeutic hypothermia, hereunder cold IV-fluid infusion, cooling catheters, transnasal evaporative cooling, extracorporeal cooling or total liquid ventilation; administration of drugs, hereunder vasopressors or vasodilators, hereunder sodium nitroprusside or nitroglycerin, thrombolytic drugs such as fibrinolytics, fluids, bicarbonate, antidotes, tissue-protecting agents and antiarrhythmic drugs, such as amiodarone; the use of ultrasound, X-ray, CT, or MR; intubation; mechanical ventilation; ventricular assist devices; surgery, including CABG surgery and valve surgery; blood transfusion; placement of external or internal pacemaker or ICD; catheter ablation; thromboendarterectomy; heart transplantation; defibrillation; transportation.

A second related method for providing resuscitation or suspended state through redistribution of cardiac output to increase supply to the brain and heart for a human in cardiac arrest or imminent cardiac arrest, comprises subjecting the patient to external chest compression while at the same time ensuring redistribution of the cardiac output accomplished by sustained abdominal compression or abdominal binding, and comprising lowering the restriction on perfusion delivered to the brain and heart through the use of a vasodilator, hereunder specifically sodium nitroprusside or nitroglycerin, hereunder repetition in intervals of 2-10 minutes, and comprising acting as a bridge to one or more of the following: ECMO; ECLS; cardiopulmonary bypass; angioplasty, including PCI and angiography; dialysis; therapeutic hypothermia, hereunder cold IV-fluid infusion, cooling catheters, transnasal evaporative cooling, extracorporeal cooling or total liquid ventilation; administration of drugs, hereunder vasopressors or vasodilators, hereunder sodium nitroprusside or nitroglycerin, thrombolytic drugs such as fibrinolytics, fluids, bicarbonate, antidotes, tissue-protecting agents and antiarrhythmic drugs, such as amiodarone; the use of ultrasound, X-ray, CT, or MR; intubation; mechanical ventilation; ventricular assist devices; surgery, including CABG surgery and valve surgery; blood transfusion; placement of external or internal pacemaker or ICD; catheter ablation; thromboendarterectomy; heart transplantation; defibrillation; transportation.

During development work of the present invention, the inventor has realized that the controlled occlusion of blood vessels that is obtained by the device of the present invention has a wider range of applications.

For instance, when performing surgery of a patient where excessive bleeding occurs, it may be inexpedient to interrupt the bleeding by traditional means (such as compression or suture of influent blood vessels), since some patients' vasculature may be too fragile and/or to sclerotic to allow such approaches. In such patients the introduction of an occlusion device, which in principle functions and is operated like the above-discussed aortic expansion member, but is dimensioned so as to be able to expand and safely occlude smaller vessels, is believed to provide a much less traumatic way of preventing blood from reaching the traumatized area where bleeding occurs.

So in a separate aspect of the invention is provided a method for stopping or reducing bleeding from tissue(s) or organ(s) during surgery of said tissue(s) or organ(s), the method comprising inserting an occlusion device into a blood vessel, which supplies said tissue(s) or organ(s) with blood, wherein said occlusion device is reversibly expanded to occlude said blood vessel and wherein the pressure exerted by the expanded occlusion device on the wall of the blood vessel is adapted to be between 1 and 2 times the vascular pressure difference across the occlusion device.

Typically, the pressure exerted by the expanded occlusion device on the wall of the blood vessel is adapted to be at most 1.5 times the vascular pressure difference across the occlusion device, such as at most 1.3, at most 1.2, and at most 1.1 times; the important goal to reach is to not traumatize the vascular wall, and in certain embodiments, the occlusion device is expanded up to exactly or just above the point where the pressure is sufficient to prevent blood from passing the device in the blood vessel.

The occlusion device will typically include or be attached to at least one vascular pressure sensor, which can determine the vascular pressure in said blood vessel. Such a pressure sensor can be positioned in said vessel between the occlusion in said vessel and said tissue(s) or organ(s) and/or positioned in the part of said vessel which is separated from said tissue(s) or organ(s) by the occlusion. In the first case, the occlusion device is sufficiently expanded when the pressure sensor can no longer measure fluctuations in vascular pressure, in the second case, the occlusion device is sufficiently expanded when the pressure exerted on the vessel's walls by the device is equal to or slightly higher than the measured vascular pressure.

In an embodiment related to the invention is provided a method for stopping or reducing bleeding from tissue(s) or organ(s), hereunder during e.g. surgery or other situations where bleeding occur of said tissue(s) or organ(s), the method comprising inserting an occlusion device (such as a device of the present invention) into a blood vessel, which supplies said tissue(s) or organ(s) with blood, wherein said occlusion device is reversibly expanded to occlude said blood vessel and wherein the pressure exerted by the expanded occlusion device on the wall of the blood vessel is adapted to be between 1 and 2 times the vascular pressure difference across the occlusion device. In this embodiment, use is made of the same pressure measurements and controls that define the device of the invention but the pressure measurements are interpreted to provide for a different use, namely to induce arrest of bleeding of an organ. The advantage is that the vessels which are occluded are not subjected to excess stress, thus preventing damage to the vessels under such operation.

DETAILED DESCRIPTION OF EMBODIMENTS OF THE INVENTION

In the following, embodiments of the invention will be described in further details with reference to the drawing in which.

Further scope of applicability of the present invention will become apparent from the following detailed description and specific examples. However, it should be understood that the detailed description and specific examples, while indicating preferred embodiments of the invention, are given by way of illustration only, since various changes and modifications within the scope of the invention will become apparent to those skilled in the art from this detailed description.

Figure 1:
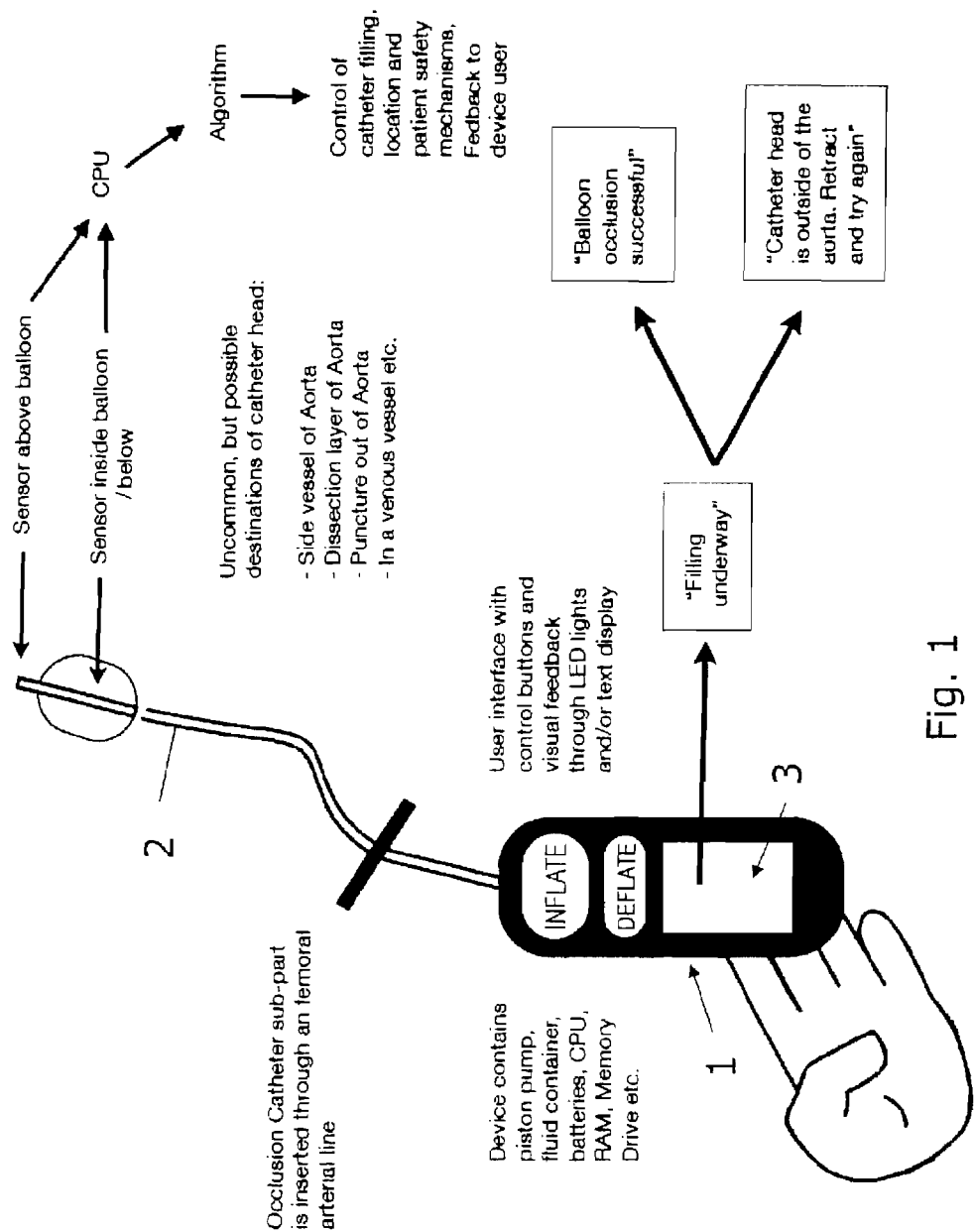
FIG. 1 illustrates a device according to the invention.
Figure 2:
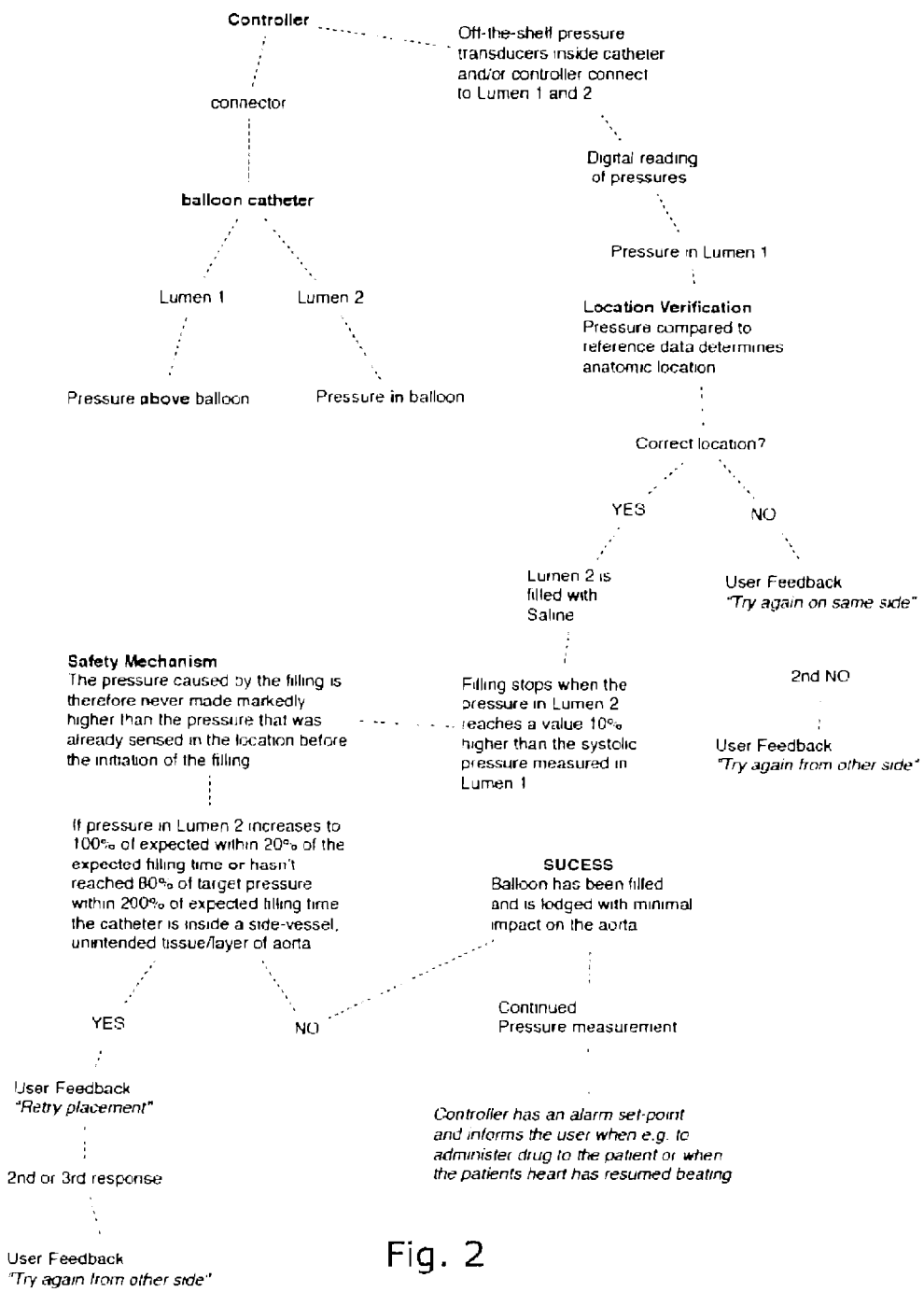
FIG. 2 illustrates functions of a device according to the invention.
Figure 3:
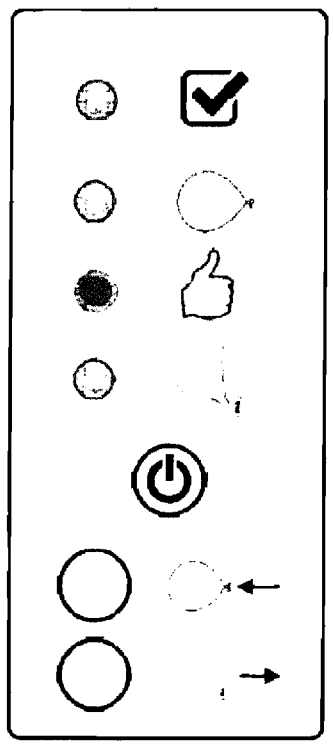
FIG. 3 illustrates a user interface.

Redistributing the cardiac output during cardiac arrest may be carried out with the device illustrated in FIG. 1, performing e.g. according to the algorithm structure illustrated in FIG. 2, and working in conjunction with a human user interface as illustrated in FIG. 3.

FIG. 1 illustrates a device 1 which contains a piston pump, a fluid container, power supply with batteries, a CPU, RAM, Memory with computer program code for the CPU, and power driven motor means for operating the piston pump.

The device is capable of providing resuscitation or suspended state through redistribution of cardiac output to increase supply to the brain and heart for a patient. The illustrated device comprises an electrically or manually controllable redistribution component in the form of an occlusion catheter sub-part 2 suitable for insertion through a femoral arterial line The occlusion catheter facilitates redistribution of the cardiac output by reducing blood flow across a balloon which is inflated in the aorta and thereby increases supply to the brain and heart.

The device is adapted for automatic operation. The CPU is configured to receive a patient data which identifies physiological and/or anatomical characteristics of the patient and to provide the electrical signal for controlling the redistribution component and/or for presenting the physiological and/or anatomical characteristics for a user based on the patient data or a standard response. In the illustrated embodiment, the occlusion catheter comprises two sensors, one being above the balloon and one being inside the balloon, or alternatively below the balloon. The sensor may particularly be pressure sensors which can provide blood pressure which herein is considered as patient data. These patient data may be generated e.g. during external cardiac compression carried out on the patient.

The signals from the sensors are transmitted to the CPU which, based on the computer program code, controls checks the location of the catheter in the aorta and the patent safety during use of the device and which controls the filing of the balloon. The CPU thereby follows a predefined reaction pattern based on the electrical signal from the sensor.

The device has a screen 3 which forms part of a user interface. The user further comprises control buttons and visual feedback through LED lights and/or text display. As illustrated in FIG. 1, the user interface may inform the user when filling is underway, and it may further inform the user about a successful balloon occlusion and thus cardiac output redistribution or alternatively that the catheter is not at the desired location in aorta.

Figure 4:
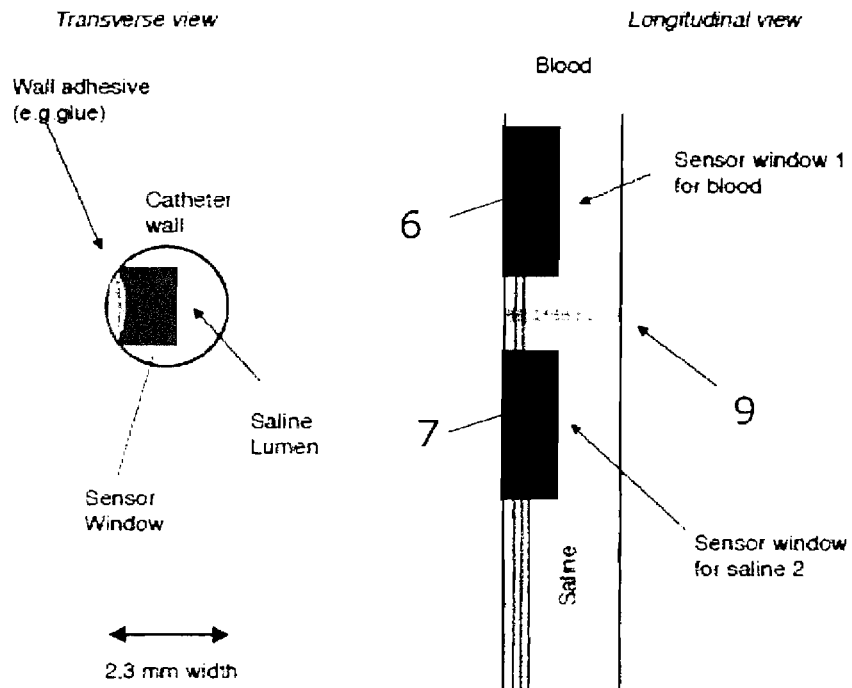
FIG. 4 illustrates a digital sensing component.

The digitally sensing catheter sub component may be designed as illustrated in FIGS. 4a and 4b. FIG. 4a is a transverse view and FIG. 4b is a longitudinal view. The structure and location of the sensors relative to the catheter may be as illustrated in FIG. 4.

The catheter body comprises an elongate tube 4 with a lumen 5 wherein saline can flow in both directions, i.e. both to and from the balloon and wherein the sensor units 6, 7 and sensor wires 8 can pass through the extent of the catheter body, as illustrated in FIG. 4. The catheter body may be constructed from PEBAX with a working length of 75 cm.

The sensors are separated by a sealing, e.g. glue, 9.

The balloon (not shown) can be made from low durometer urethane, with a wall thickness of 0.05 mm, an overall length of 30 mm, and a diameter from 20-40 mm depending on filling degree, having a burst pressure of at least 500 mmHg.

The balloon may be configured in size to occlude the aorta of the patient.

The sensors may pressure sensors of the type MEMS, e.g. MEMS pressure sensor, MEM2000, Metallux Switzerland.

Figure 5:
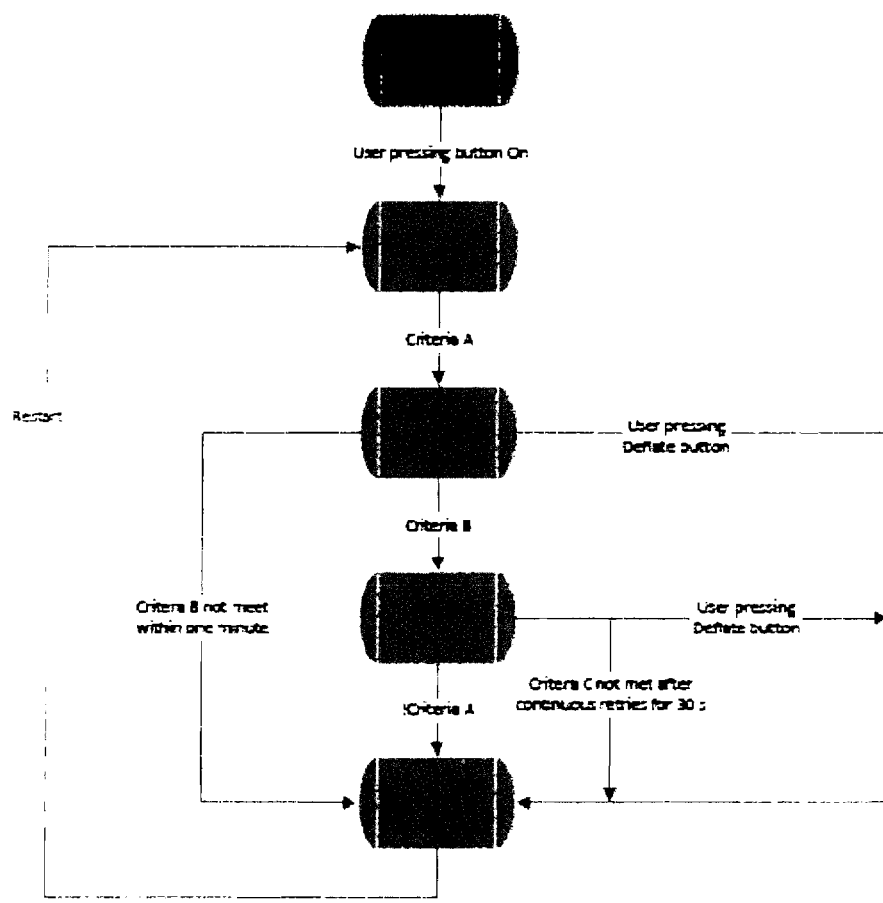
FIG. 5 illustrates software functions.
Figure 6:
FIGS. 6-7 illustrate an aortic expansion member.
Figure 7:
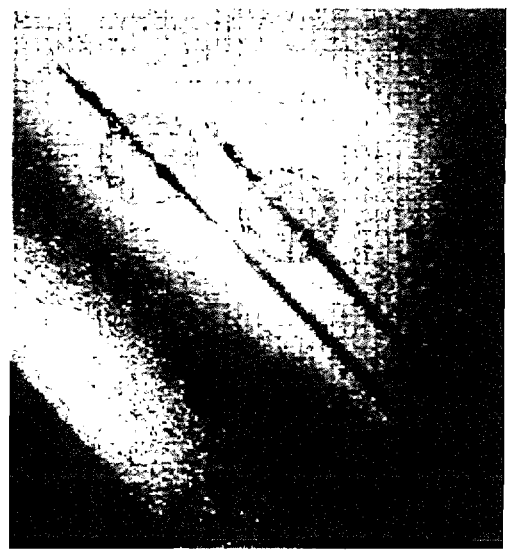
Figure 8:
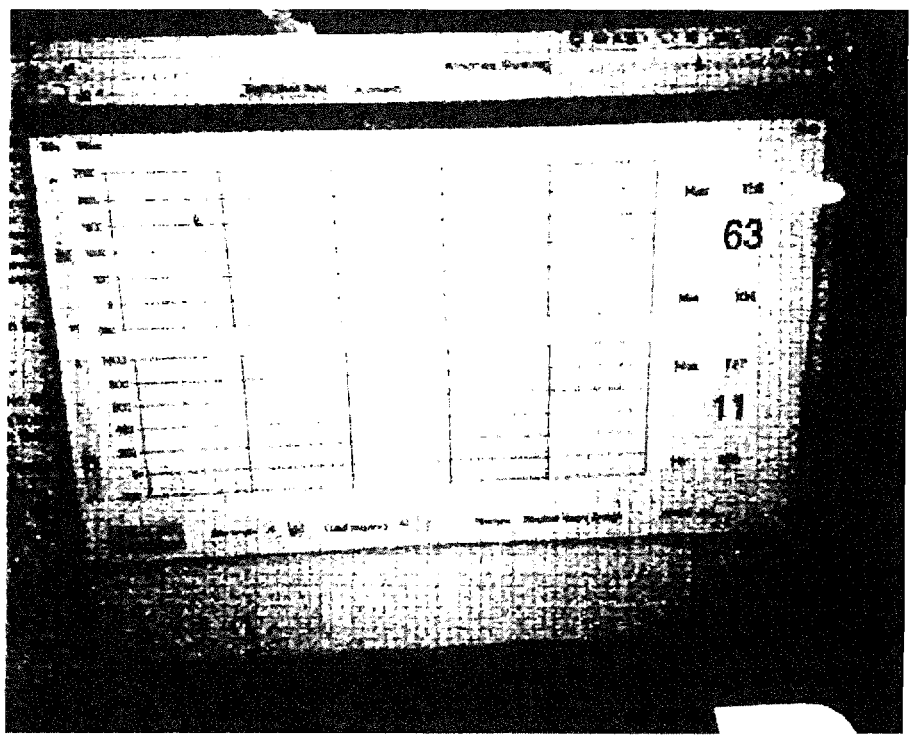
FIG. 8 illustrates a user interface screen on a PC.
Figure 9:
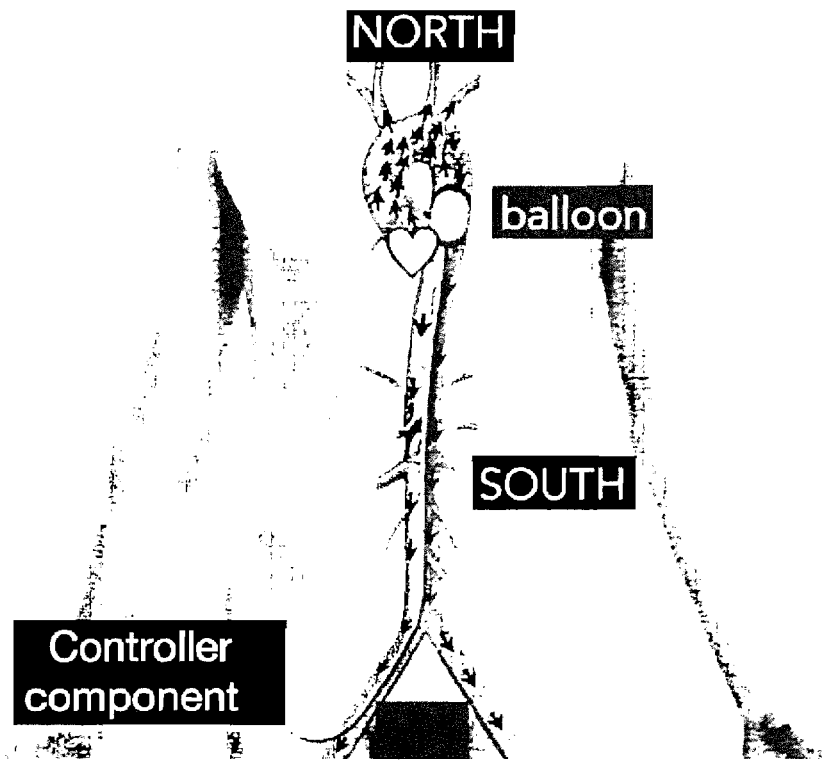
FIG. 9 illustrates placement in a human being.

The sensors can be interfaced with a print circuit board via USB. The USB connection allows for the signal to be processed digitally and used as input for the software algorithms as illustrated in FIG. 2 and FIG. 5.

The device further comprises a controller component. The controller component may contain a membrane keyboard with LEDs for user interface, integrated circuit, a pump, hereunder e.g. a piston pump or roller pump, battery, and any other additional component for controlling, powering, or operating the device in accordance with the invention.

Figure 11:
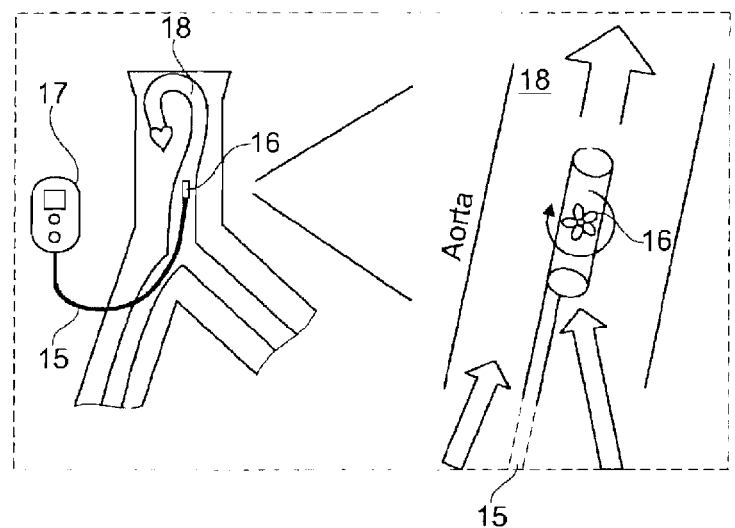
FIG. 11 illustrates a retrograde pump.

Another embodiment of the invention is illustrated in FIG. 11. In this embodiment, the catheter component 15 of the device further compromises a retrograde pump 16 controlled by controlled by communication with the CPU contained in the external part 17 of the device. The pump could be a brushless type pump such as brushless EC6 motor from Maxon, Maxon precision motors Inc. The pump is located in the aorta 18.

The catheter subpart may be inserted into the aorta of the patient by locating and puncturing the femoral artery and by inserting the device through the defined opening. The device could be used for the puncturing and placement procedures and these procedures may be integrated into the device. The device can aid the user from unintended harmful events occurring to the patient through the active security mechanism modes illustrated in FIG. 5.

Figure 10:
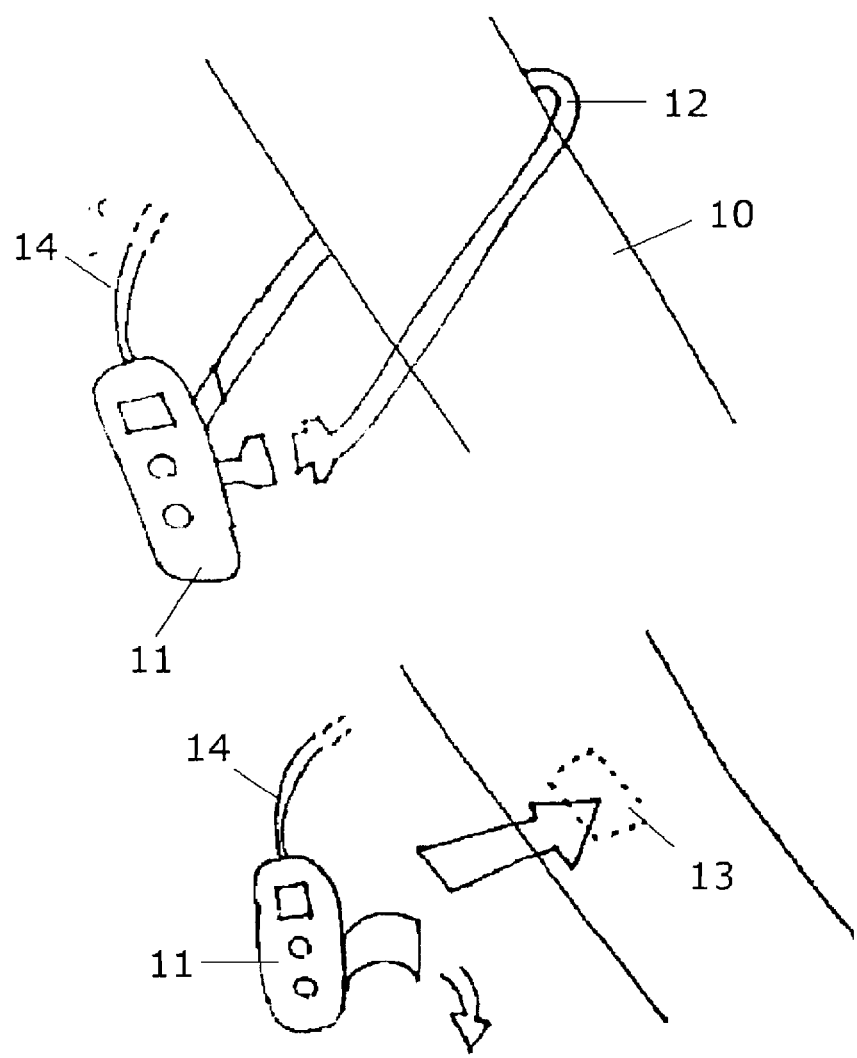
FIG. 10 illustrates attachment of the device to a limp of a patient.

The controller component of the device can be attached or fixed to the leg 10 of a patient through e.g. a wraparound leg belt or an adhesive fixation pad. FIG. 10 illustrates an embodiment where the device 11 is strapped to the patient with a strap 12 or fixed to the patient by an adhesive 13. In both embodiments, the catheter 14 extends into the aorta through a sealed port.

In another embodiment of the invention, the device can be implanted into a patient. This device may function through wireless coordination and electricity transfer between the device and a pacemaker, ICD or similar implantable cardiovascular diagnostic or therapeutic medical device, as illustrated in FIGS. 12a-12e.

Figure 12A:
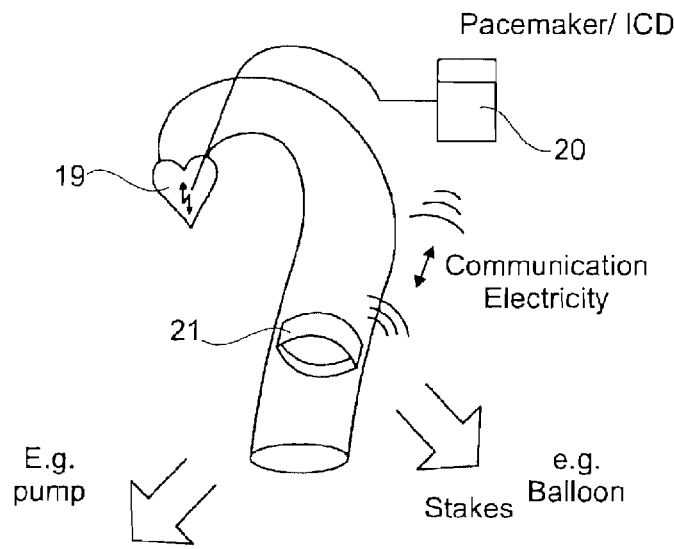
FIGS. 12a-12e illustrate an implanted device.
Figure 12B:
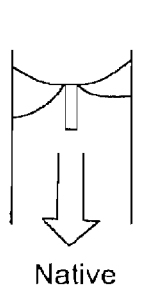
Figure 12C:
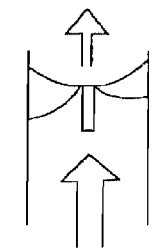
Figure 12D:
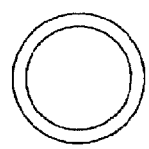
Figure 12E:
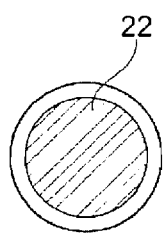

FIG. 12a illustrates a heart 19 with a pacemaker/ICD 20 communicating signals with a redistribution component 21. In FIGS. 12b and 12c, the redistribution component is a pump, and in FIGS. 12d and 12e, the redistribution component is an occlusion balloon 22.

In another embodiment of the invention, the device functions as part of a robotic puncture and insertion system, further decreasing the room for user error.

Expectedly, the system includes a variation of the above configurations and modes.

EXAMPLE 1

Operation of a Device of the Invention

The device is started by pressing the button ON or it is started by unpacking the device e.g. by releasing an attachment to the electrical circuit between device and battery. The user uncovers the catheter and inserts the catheter into the patient. Once the user has completed the procedure, the user presses INFLATE, and the system enters the Position verification mode.

Position Verification Mode

When the criteria for the correct position is met, the indicator "Position correct ✓" starts blinking green and the indicator "Pumping ☉" starts blinking yellow, then the system enters Actuator (inflation) mode.

If the correct position is not achieved or if the correct position is lost, then indicator "Pumping ☉" stops blinking, an alarms sounds and "Retry placement x" starts blinking, until INFLATE is pressed again.

Actuator (Inflation) Mode

The actuator is activated and the balloon is inflated. When the criteria for a filled balloon is reached the actuator is stopped, the indicator "Pumping ☉" stops blinking yellow and Self-adjustment mode is entered.

If the criteria are not met after one minute, or the user presses the DEFLATE button, the Deflation mode is entered followed by "Retry placement x" starting to blink and staying lit until INFLATE is pressed again.

Self-Adjustment Mode

The indicator "Balloon filled—♦" starts blinking green. The self-adjustment mode regulates the pressure in the balloon to a correct pressure according to the criteria.

If the criteria can't be held, an alarm sounds, the deflation mode is entered followed by "Retry placement x" starting to blink until INFLATE is pressed again, or if the user presses the DEFLATE button, the Deflation mode is entered.

Deflation Mode

The indicator "Pumping ☉" starts blinking yellow. The actuator is activated and the balloon is deflated.

When the balloon is deflated "Balloon deflated—•" starts blinking blue until the user presses INFLATE again.

Glossary

P1 is Pressure sensor 1, as illustrated in FIG. 1, and P2, is pressure sensor 2.

Positioning Criteria

The maximum pressure measured by P1 is above 15 mmHg and has a delta between the max and min pressure measured higher than 5 mmHg. 50 Hz.

Filling Criteria

P2 reach the pressure measured by P1×1.20. 50 Hz

Self-Adjustment Criteria

P2 is still within the following range: (P1×1.10)-(P1×1.30). 0.1 Hz.

The device may signal the user with the following visual and/or auditory signals:

Message A: "Filling. Continue CPR."
Message B: "Retry placement. Balloon is now empty."
Message C: "Aorta Occlusion success."
Message D: "Deflation done."

EXAMPLE 2

Simulation Experiment

A model of the human ascending aorta, aortic arch, and common femoral arteries was produced in silicone rubber. The model was submerged in water and internal pressure (100 mmHg) in the model was applied via a connected water column. Chest compressions were simulated by manually applying pressure to an attached balloon.

The test device was inserted from an opening in the part of the model corresponding to the left common femoral artery so as allow the tip to reach a position corresponding to just proximal of the renal arteries. The occlusion balloon was inflated while recording MEMS pressure sensor data from the tip of the catheter and from the interior of the balloon compartment.

It was demonstrated that the positioning and occlusion of the redistribution catheter can be controlled and verified through the use of software-hardware integration mechanisms. For example, measuring the correct pressures during filling corresponding to the catheter tip being in the aorta (and e.g. not misplaced in the renal artery) allows pressure control of the filling of the balloon as a function of the pressures intended to be countered. In other words, if the catheter is not placed in the correct position, filling of the balloon counter the aortic pressure and has the consequence that the pressure measured at the tip drops to zero instead of remaining at the level of the aortic pressure.

EXAMPLE 3

In vivo Experiment

A prototype device was tested in two pilot animal trials. The animals were healthy Danish farm pigs of 30-38 kg, which were sedated using pentobarbital (Mebumal) 50 mg/ml, 6 mg/kg/h and ketamine (Ketaminol vet) 100 mg/ml, 15 mg/kg/h. The animals further were administered 2000 unites of unfractionated heparin.

The animals were mechanically ventilated and oxygen levels were set to 23% oxygen prior to cardiac arrest. During the experiment the animals were continuously supplied with saline (0.9% NaCl) at an infusion speed of 2 l/h.

Cardiac arrest was induced by applying 9 V DC directly to the heart by electrodes introduced via the right jugular vein. Cardiac arrest was defined as a systolic blood pressure <25 mmHg for more than 5 seconds.

ROSC was defined as a pulsatile rhythm with a systolic aortic blood pressure >60 mm Hg maintained for at least 5 min.

Arterial blood pressure, venous blood pressure and heart rate were measured with intravascular gauges in the aortic arch through the right carotid artery at the junction with the aorta, and the right jugular vein entering the central vena cava.

Pig no. 1 had the following baseline values prior to induction of cardiac arrest: heart rate 85 bpm, arterial blood pressure 98/63 mmHg, venous blood pressure 15 mmHg. After the induction of cardiac arrest, the pig was left in no-flow state for 1 min. Hereafter mechanical chest compressions were delivered with the LUCAS 2 device (Physiocontrol) continued for an additional 5 min. After the pig had sustained a cardiac arrest for a total of 6 min, the prototype device was introduced to the aorta through the right femoral artery. The parameters after the 6 min. of cardiac arrest were measured as the following: Heart rate 0 bmp, with a mechanical setting at 100 compressions/min, blood pressure was 34/23 mmHg, and central venous pressure was 20 mmHg. Hereafter the prototype device was turned on and the effect were left to take hold for 1 min. The values were measured to the following regarding 1 min of sustained use of the prototype device: Heart rate 0, with a mechanical setting at 100/compressions/min, central arterial blood pressure was 59/28 mmHg, central venous pressure was 22 mmHg.

The use of the prototype device demonstrated an increase of the central arterial pressure, and thus also of the coronary perfusion pressure and cerebral perfusion pressure, from systolic 34 mmHg to 59 mmHg, and a sustained venous pressure going from 20 to 22 mmHg. The coronary perfusion pressure, the central parameter in cardiac resuscitation, is calculated as the difference between the systolic central arterial pressure and the central venous pressure. We are thus able to demonstrate an increase of the coronary perfusion pressure with 164%.

Pig no. 2 was subjected to the same conditions as Pig no. 1, but cardiac arrest was effected by inducing blood loss (700 ml) by bleeding from the right femoral artery prior to instigation of the treatment.

Pig no. 2 had the following baseline values prior to induction of cardiac arrest: heart rate 105 bpm, arterial blood pressure 96/42 mmHg, venous blood pressure 12 mmHg. After blood loss the values were: heart rate: 93 bpm, arterial blood pressure: 35/20 mmHg, central venous pressure: 10 mmHg. Treatment was commenced. After 1 minute of treatment the values had changed to: heart rate: 95 bpm, arterial blood pressure: 55/30 mmHg, central venous blood pressure: 10 mmHg.

Hence, by using the prototype of the invention, it was achieved to obtain a 57% increase the arterial blood pressure, whereas an 80% increase in coronary perfusion pressure was obtained.

The invention claimed is:

1. A device for providing resuscitation or suspended state through redistribution of cardiac output to increase supply to the brain and heart for a patient, the device comprising
   an electrically or manually controllable occlusion device in the form of an aortic expansion member attachable to the patient and being configured to interact with the patient to provide redistribution of the cardiac output to increase supply to the brain and heart, and an inflation means connected to the aortic expansion member for expanding the aortic expansion member, and the aortic expansion member following a predefined reaction pattern based on an electrical signal, and
   computer means configured to:
      receive a patient data which identifies physiological and/or anatomical characteristics of the patient; and
      provide the electrical signal for controlling the aortic expansion member and/or for presenting the physiological and/or anatomical characteristics for a user based on the patient data;
   an adaptable tissue protection mechanism configured to 1) determine a blood pressure or blood flow present in a blood vessel of the patient 2) determine a characteristic of the aortic expansion member defining a degree of expansion of the aortic expansion member based on the determined blood pressure or blood flow, and 3) provide an electrical signal for controlling the inflation means in accordance with the determined aortic expansion member characteristics so as to avoid damage to the patient.

2. The device according to claim 1, where the computer means comprises memory means having stored therein a predefined definition of the electrical signal as a response to the patient data.

3. The device according to claim 1, comprising patient data generation means configured to generate patient data during external cardiac compression carried out on the patient, the patient data generation means configured to generate the patient data by sensing biosignals from the patient.

4. The device according to claim 3, where the patient data generation means is configured to sense biosignals from a blood vessel or a tissue compartment.

5. The device according to claim 1, wherein the inflation means is adapted to be capable of being operated manually by a user.

6. The device according to claim 1, wherein the inflation means is adapted to be capable of being operated automatically.

7. The device according to claim 1, where the electrical signal specifies a degree of expansion of the aortic expansion member, a timing of expansion of the aortic expansion member, an upper limit of expansion of the aortic expansion member, a duration of expansion of the aortic expansion member, and/or a timing of contraction of the aortic expansion member.

8. The device according to claim 7, wherein the inflation means is controlled based on the patient data in combination with the electrical signal.

9. The device according to claim 1, where the inflation means comprises a piston or roller pump.

10. The device according to claim 1, further comprising at least one first sensor capable of determining a biosignal which is characteristic for aorta of the patient and an electronic circuit configured to verify a position of the expansion member in aorta based on the biosignal.

11. The device according to claim 10, where the at least one first sensor comprises a pressure sensor.

12. The device according to claim 10, where the first sensor is located on the aortic expansion member to determine the biosignal in a position distal to the aortic expansion member.

13. The device according to claim 12, where the device is configured to use data from the first sensor in combination with data from sensors located at other locations.

14. The device according to claim 13, where at least one of the other sensors is located on the aortic expansion member to determine the biosignal in a position proximal to the aortic expansion member.

15. The device according to claim 10, which is configured to determine whether the aortic expansion member is located in a position selected from a group consisting of: a pulsating vessel in accordance with being the aorta of the patient, a pulsating vessel not in accordance with being the aorta, a pulsating vessel being indeterminate as the aorta of the patient, a venous vessel, a tissue compartment not being a blood vessel and a tissue compartment indeterminate in location.

16. The device according to claim 10, further comprising a second sensor inside the aortic expansion member or proximal to the expansion member.

17. The device according to claim 10, wherein the device is configured with a feedback loop receiving data from at least one of the first and second sensor, to control the filling of the aortic expansion member.

18. The device according to claim 1, further comprising a first failsafe mechanism, configured to determine a pressure in the aortic expansion member and to determine a volume of the aortic expansion member, to determine a ratio between the pressure and the volume, and to compare the ratio with an upper and lower threshold value, and to execute a control sequence including stopping of further inflation of the aortic expansion member or deflation of the aortic expansion member.

19. The device according to claim 1, further comprising a user interface for use of selectable operation of the inflation means.

20. The device according to claim 1, comprising a halt interface allowing manually selectable deflation of the aortic inflation member.

21. The device according to claim 20, where the halt interface is configured to execute the selectable deflation over a predefined number of seconds.

22. The device according to claim 1, comprising a patient state monitor configured to determine a biosignal representing Return of Spontaneous Circulation (ROSC), and to control deflation of the aortic expansion member based on the determined signal.

23. The device according to claim 1, further comprising an electronic human interface with a graphical or audio user interface configured to provide instructions or information related to the location and degree of filling of the aortic expansion member in the aorta of the patient, said human interface optionally being attachable in a fixed position on a patient.

24. The device according to claim 1, further comprising at least one sensor for determining pressure, flow, $O_2$ saturation or concentration, and/or volume data significant for pressure, flow and/or volume of a fluid inside the aortic expansion member or inside a blood vessel or tissue of the patient.

25. The device according to claim 24, where the computer means is configured to compare the pressure, flow and/or volume data with reference input data and based on the comparison to verify a position of the aortic expansion member in the body.

26. The device according to claim 24, where the computer means is configured to determine the size and type of blood vessel by analyzing the pressure flow and/or volume data continuously.

27. The device according to claim 24, where the computer means is configured to activate a failsafe for some verified positions in the body or limits based on sensor data analysis, thereby stopping the aortic expansion member interaction with the patient, the expansion of the aortic member or initiation of contraction of the aortic member.

28. The device according to claim 24, wherein an interactive human user guide is configured to provide information related to a position of the aortic expansion member in the patient, the information being determined based on the pressure, flow and/or volume data.

29. The device according to claim 1, where the patient data includes parameters selected from the group consisting of: aortic blood pressure, aortic blood flow, duration of cardiac arrest, expiratory $CO_2$, ECG, blood pressure, compression rate and depth, pulse, respiratory frequency, cardiac output redistribution degree, aortic $O_2$ saturation or concentration, cerebral or peripheral saturation, temperature, fluid administered, pharmaceuticals administered, biochemical data, and ultrasound imaging.

30. The device according to claim 1, where the aortic expansion member comprises an aortic occluding balloon.

31. The device according to claim 30, further compromising means for filling the aortic occluding balloon with a liquid or a gas.

32. The device according to claim 31, further comprising a handheld unit comprising the computer means and the filling means and being attachable to the aortic occluding balloon.

33. The device according to claim 31, further comprising a human interface unit comprising the filling means and being attachable to the aortic occluding balloon.

34. The device according to claim 32, wherein the aortic occluding balloon is attached to the handheld unit.

35. The device according to claim 33, wherein said human interface is configured to be attachable in a fixed position on said patient.

36. The device according to claim 33, wherein said human interface is integrated with the human interface defined in claim 23 or the handheld unit defined in claim 32.

37. The device according to claim 1, further comprising a component attachable to the patient and being configured to administer fluids and drugs to the patient.

38. The device according to claim 1, further comprising means for a self-test system, and usage event data recording.

39. The device according to claim 1, wherein the computer means communicates with at least one other therapeutic and/or monitoring device so as to allow coordination of the operation of said therapeutic devices and the device according to claim 1.

40. The device according to claim 39, wherein the at least one other therapeutic and/or monitoring device is selected from a cardiac resynchronization therapy device, a cardioverter-defibrillator, and a cardiac pacemaker.

41. The device according to claim 1, wherein the damage to the patient, which is avoided, is caused by the expansion of the aortic expansion member.

42. The device according to claim 1, wherein the damage to the patient, which is avoided, is damage caused by incorrect positioning of the aortic expansion member.

43. A method for providing resuscitation or suspended state in a human cardiac arrest patient, said method comprising subjecting the patient to heart massage (chest compression) while at the same time ensuring redistribution of the cardiac output to preferentially supply blood to the brain and the heart, wherein redistribution is accomplished by occlusion of the aorta caudal to the left subclavian artery by introducing a device according to claim 1 into the aorta, and subsequently decreasing or interrupting the blood flow distal to the aortic expansion member by expanding the aortic expansion member of said device.

44. The method according to claim 43, wherein the aortic expansion member is expanded in a controlled manner in response to measurement(s) that indicate the degree of occlusion and correct placement of said device in the patient's aorta.

45. The method according to claim 44, wherein said measurement(s) is/are selected from the group consisting of:
duration of expansion aortic expansion member usage;
blood flow passing by the aortic expansion member;
blood pressure distal of the aortic expansion member, or combined with blood pressure proximal to the aortic expansion member;
aortic $O_2$ saturation distal of, and preferably in close proximity to, the aortic expansion member, or combined with arterial $O_2$ saturation proximal of the aortic expansion member.

46. The method according to claim 43, wherein the redistribution is temporarily interrupted at regular or irregular intervals so as to ensure sufficient perfusion of all parts of the body of the patient.

47. The method according to claim 43, which acts during or as a bridge to one or more of therapeutic hypothermia; angioplasty, including PCI and angiography; dialysis; administration of drugs such as vasopressors, thrombolytic drugs such as fibrinolytics, fluids, bicarbonate, antidotes, and antiarrhythmic drugs; the use of ultrasound, X-ray, CT, or MR; intubation; mechanical ventilation; ventricular assist devices; heart transplantation, including artificial heart transplantation; surgery, including CABG surgery and valve surgery; blood transfusion; placement of external or internal pacemaker or ICD; catheter ablation; thromboendarterectomy; defibrillation; transportation; ECMO; ECLS and cardiopulmonary bypass.

48. A method for providing resuscitation or suspended state in a human cardiac arrest patient according to claim 43, wherein redistribution is accomplished by occlusion of the aorta caudal to the left subclavian artery by introducing said device into the aorta via the femoral artery.

49. A method for stopping or reducing bleeding from tissue(s) or organ(s), the method comprising: inserting an occlusion device into a blood vessel, which supplies said tissue(s) or organ(s) with blood, wherein said occlusion device is reversibly expanded to occlude said blood vessel and wherein the pressure exerted by the expanded occlusion device on the wall of the blood vessel is adapted to be between 1 and 2 times the vascular pressure difference across the occlusion device, wherein the occlusion device is part of a device defined in claim 1, wherein the aortic expansion member is adapted to be able to fit into other blood vessels than the aorta.

50. The method according to claim 49, wherein the pressure exerted by the expanded occlusion device on the wall of the blood vessel is adapted to be at most 1.9 times the vascular pressure difference across the occlusion device, such as at most 1.8, at most 1.7, at most 1.6, at most 1.5, at most 1.4, at most 1.3, at most 1.2 and at most 1.1 times.

51. The method according to claim 49, wherein the occlusion device includes or is attached to at least one vascular pressure sensor, which can determine the vascular pressure in said blood vessel.

52. The method according to claim 51, wherein the at least one pressure sensor is positioned in said vessel between the occlusion in said vessel and said tissue(s) or organ(s) and/or is positioned in the part of said vessel which is separated from said tissue(s) or organ(s) by the occlusion.

53. The method according to claim 49, wherein said method is used during a surgery or other situations where bleeding occurs in said tissue(s) or organ(s).

54. A device for providing resuscitation or suspended state through redistribution of cardiac output to increase supply to the brain and heart for a patient, the device comprising
an electrically or manually controllable aortic expansion member attachable to the patient and being configured to interact with the patient to provide redistribution of the cardiac output to increase supply to the brain and heart by occluding the aorta, and an inflation means connected to the aortic expansion member for expanding the aortic expansion member, and the aortic expansion member following a predefined reaction pattern based on an electrical signal, and
computer means configured to:
receive a patient data which identifies physiological and/or anatomical characteristics of the patient; and
provide the electrical signal for controlling the aortic expansion member and/or for presenting the physiological and/or anatomical characteristics for a user based on the patient data, and
wherein the electrical signal specifies 1) a degree of expansion of and/or 2) a timing of expansion of and/or 3) duration of expansion of and/or 4) a timing of contraction of the aortic expansion member, and wherein the device comprises a) means for specifying a degree of expansion of the expansion member and/or b) means for timing of the expansion of the expansion member and/or c) means for determining duration of expansion of the expansion member and/or d) means for timing of contraction of the expansion member.

55. The device according to claim 54, wherein said means defined in a-d are controlled based on the patient data in combination with the predefined reaction pattern or with the electrical signal.

* * * * *